US00PP13094P2

(12) United States Plant Patent
Davino, Jr.

(10) Patent No.: US PP13,094 P2
(45) Date of Patent: Oct. 15, 2002

(54) CHRYSANTHEMUM PLANT NAMED 'DREAMY YOLINDA'

(75) Inventor: Louis Davino, Jr., Hightstown, NJ (US)

(73) Assignee: Yoder Brothers, Inc., Barberton, OH (US)

( * ) Notice: Subject to any disclaimer, the term of this patent is extended or adjusted under 35 U.S.C. 154(b) by 1 days.

(21) Appl. No.: 09/837,587

(22) Filed: Apr. 19, 2001

(51) Int. Cl.[7] ..... A01H 5/00
(52) U.S. Cl. ..... Plt./289
(58) Field of Search ..... Plt./288, 289

*Primary Examiner*—Howard J. Locker
(74) *Attorney, Agent, or Firm*—C. A. Whealy

(57) ABSTRACT

A distinct cultivar of Chrysanthemum plant named 'Dreamy Yolinda', characterized by its upright plant habit; freely branching growth habit; uniform and freely flowering habit; decorative-type inflorescences; and light yellow-colored ray florets.

1 Drawing Sheet

BACKGROUND OF THE INVENTION

The present invention relates to a new and distinct cultivar of Chrysanthemum plant, botanically known as *Chrysanthemum×morifolium* and hereinafter referred to by the name 'Dreamy Yolinda'.

The new Chrysanthemum is a naturally-occurring whole plant mutation of the Chrysanthemum cultivar Linda, disclosed in U.S. Plant Pat. No. 8,294. The new Chrysanthemum was discovered and selected by the Inventor as a single flowering plant within a population of flowering plants of the parent cultivar in October, 1997 in a controlled environment in Hightstown, N.J. The selection of this plant was based on its unique ray floret color.

Asexual reproduction of the new cultivar by terminal cuttings taken in a controlled environment in Gainesville, Fla. since December, 1997, has shown that the unique features of this new Chrysanthemum are stable and reproduced true to type in successive generations.

SUMMARY OF THE INVENTION

The cultivar Dreamy Yolinda has not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Dreamy Yolinda'. These characteristics in combination distinguish 'Dreamy Yolinda' as a new and distinct cultivar:

1. Upright plant habit.
2. Freely branching, dense, full plants.
3. Uniform and freely flowering.
4. Decorative-type inflorescences.
5. Light yellow-colored ray florets.

Compared to plants of the parent cultivar Linda, plants of the new Chrysanthemum flower earlier and differ in ray floret color.

BRIEF DESCRIPTION OF THE PHOTOGRAPHS

The accompanying photographs illustrate the overall appearance of the new Chrysanthemum. These photographs show the colors as true as it is reasonably possible to obtain in colored reproductions of this type. Colors in the photographs may differ slightly from the color values cited in the detailed botanical description which accurately describe the colors of the new Chrysanthemum.

The photograph at the top of the sheet comprises a side perspective view of a typical flowering plant of 'Dreamy Yolinda'.

The photograph at the bottom of the sheet comprises a close-up view of typical inflorescences of the cultivar 'Dreamy Yolinda'.

DETAILED BOTANICAL DESCRIPTION

In the following description, color references are made to The Royal Horticultural Society Colour Chart except where general terms of ordinary dictionary significance are used. The following observations and measurements describe plants grown in Salinas, Calif., under conditions which approximate those generally used in commercial garden Chrysanthemum production. One rooted cutting was planted in a 15-cm container in July, 2000 and plants were grown under natural season conditions. Plants were not pinched, that is, the terminal apex was not removed to enhance branching. Measurements and numerical values represent averages for typical flowering plants.

Botanical classification: *Chrysanthemum×morifolium* cultivar Dreamy Yolinda.

Commercial classification: Decorative-type garden Chrysanthemum.

Parentage: Naturally-occurring whole plant mutation of *Chrysanthemum×morifolium* cultivar Linda, disclosed in U.S. Plant Pat. No. 8,294.

Propagation:

*Type.*—Terminal tip cuttings.

*Time to initiate roots.*—About four days at 21° C.

*Time to produce a rooted cutting.*—About ten days at 21° C.

*Root description.*—White, fine and fibrous.

*Rooting habit.*—Freely branching.

Plant description:

*Appearance.*—Perennial herbaceous decorative-type garden Chrysanthemum. Inverted triangle; upright plant form. Stems initially upright, then somewhat outwardly spreading giving a uniformly mounded appearance to the plant. Freely branching with about 11 lateral branches per plant.

*Plant height.*—About 22 cm.

*Plant diameter.*—About 28 cm.

*Lateral branches.*— Length: About 18 cm. Diameter: About 5 mm. Internode length: About 1.6 cm. Aspect: Upright and somewhat outward. Texture: Pubescent. Color: 144A.

*Foliage description.*— Leaf arrangement: Alternate. Length: About 5.4 cm. Width: About 4.1 cm. Apex: Cuspidate to mucronate. Base: Attenuate. Margin: Palmately lobed, sinuses mostly divergent. Texture: Both surfaces, pubescent; veins prominent on lower surface. Color: Young foliage upper surface: 147A. Young foliage lower surface: 147B. Mature foliage upper surface: 147A. Mature foliage lower surface: 147B. Venation, both surfaces: 146B. Petiole length: About 2.1 cm. Petiole diameter: About 2.5 mm. Petiole color, both surfaces: 146B to 146C.

Inflorescence description:

*Appearance.*—Decorative-type inflorescence form with elongated oblong-shaped ray florets. Inflorescences borne on terminals above foliage, arising from leaf axils. Disk and ray florets arranged acropetally on a capitulum. About 11 inflorescences per lateral; about 121 inflorescences per plant.

*Flowering response.*—Under natural season conditions, plants flower in late September to early October in the Northern Hemisphere and continue to flower for at least three weeks depending on weather conditions.

*Inflorescence bud* (*before showing color*).— Height: About 5 mm. Diameter: About 7 mm. Phyllary color: 143A.

*Inflorescence size.*— Diameter: About 4.7 cm. Depth (height): About 1.9 cm. Disc diameter: About 2 mm or less, inconspicuous. Receptacle diameter: About 6.5 mm.

*Ray florets.*— Shape: Elongated oblong. Length: About 2.2 cm. Corolla tube length: About 6 mm. Width: About 4 mm. Apex: Acute, emarginate or denate. Margin: Entire. Texture: Smooth, glabrous, satiny. Orientation: Initially upright and incurved, then perpendicular to the peduncle and concave. Number of ray florets per inflorescence: About 219. Color: When opening, upper and lower surfaces: Close to 4A. Opened inflorescence, upper surface: Close to 4B to 4C; fading to close to 4C to 4D. Opened inflorescence, lower surface: Close to 4C to 4D.

*Disc florets.*— Shape: Tabular, apex dentate. Length: About 4 mm. Width: Apex: About 1.25 mm. Base: About 1 mm. Number of disc florets per inflorescence: Less than 10. Color: Immature: 154A. Mature: Apex: 9A. Mid-section: 154D to 155D. Base: 155D.

*Peduncle.*— Aspect: Flexible, angled about 45° from the stem. Length: First peduncle: About 7.1 cm. Fourth peduncle: About 11.4 cm. Diameter: About 2 mm. Texture: Pubescent. Color: Close to 144B.

*Reproductive organs.*— Androecium: Present on disc florets only. Anther color: 9A. Pollen: None. Gynoecium: Present on both ray and disc florets.

*Seed.*—Seed production has not been observed.

Disease resistance: Plants of the new chrysanthemum have not been shown to be resistant to pathogens common to Chrysanthemums.

Garden performance: Plants of the new Chrysanthemum have been observed to be tolerant to rain and wind.

It is claimed;

1. A new and distinct cultivar of Chrysanthemum plant named 'Dreamy Yolinda', as illustrated and described.

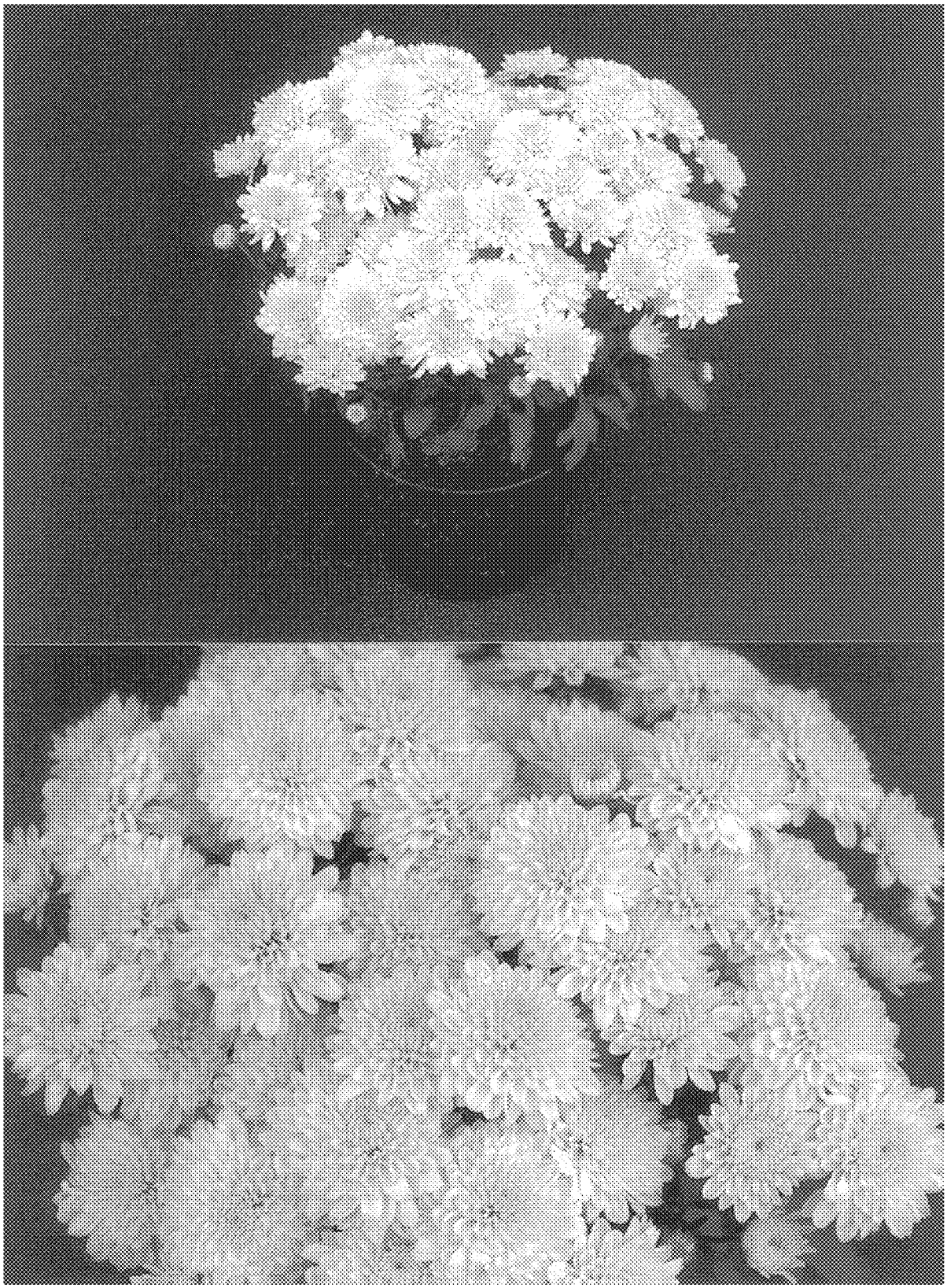

* * * * *